United States Patent [19]
Wong

[11] Patent Number: 6,046,039
[45] Date of Patent: Apr. 4, 2000

[54] METHODS FOR PRODUCING PARTIALLY DIGESTED RESTRICTION DNA FRAGMENTS AND FOR PRODUCING A PARTIALLY MODIFIED PCR PRODUCT

[75] Inventor: Kwong-Kwok Wong, Richland, Wash.

[73] Assignee: Battelle Memorial Institute, Richland, Wash.

[21] Appl. No.: 09/138,041

[22] Filed: Aug. 19, 1998

[51] Int. Cl.$^7$ ..................................................... C12P 17/34
[52] U.S. Cl. ........................... 435/91.1; 435/6; 435/91.2; 436/501; 536/25.3
[58] Field of Search ............................ 435/6, 91.1, 91.2; 436/501; 536/25.3; 935/77.78

[56] References Cited

U.S. PATENT DOCUMENTS

| | | | |
|---|---|---|---|
| 5,316,948 | 5/1994 | Pless ........................................ | 435/91.2 |
| 5,487,985 | 1/1996 | McClelland et al. ................... | 435/91.2 |
| 5,759,778 | 6/1998 | Li et al. .................................. | 435/6 |
| 5,821,356 | 10/1998 | Khan et al. ........................... | 536/26.26 |

OTHER PUBLICATIONS

PCR with 5-methyl-dCTP replacing dCTP, KK Wong and M McClelland, Nucleic Acids Research, vol. 19, No. 5, 1991, pp. 1081–1085.

Partial Digestion with Restrictin Enzymes of Ultraviolet–Irradiated Human Genomic DNA: A Method for Identifying Restriction Site Polymorphisms, C Nobile and G Romeo, Genomics 3, 272–274 (1988).

New cloning vectors and techniques for easy and rapid restriction mappping, KD Tartof and CA Hobbs, Gene 67, 169–182 (1988).

Control of partial digestion combining the enzymes dam methylase and MboI, JD Hoheisel, D Nizetic and H Lehrach, Nucleic Acids Research, vol. 17, No. 23 (1989), pp. 9571–9582.

Determination of Fragment Order through Partial Digests and Multiple Enzyme digests, KJ Danna, Methods in Enzymology, vol. 65, pp. 449–467 (1980).

*Primary Examiner*—Ardin H. Marschel
*Attorney, Agent, or Firm*—Paul W. Zimmerman

[57] ABSTRACT

The present invention is an improved method of making a partially modified PCR product from a DNA fragment with a polymerase chain reaction (PCR). In a standard PCR process, the DNA fragment is combined with starting deoxynucleoside triphosphates, a primer, a buffer and a DNA polymerase in a PCR mixture. The PCR mixture is then reacted in the PCR producing copies of the DNA fragment. The improvement of the present invention is adding an amount of a modifier at any step prior to completion of the PCR process thereby randomly and partially modifying the copies of the DNA fragment as a partially modified PCR product. The partially modified PCR product may then be digested with an enzyme that cuts the partially modified PCR product at unmodified sites thereby producing an array of DNA restriction fragments.

17 Claims, 3 Drawing Sheets

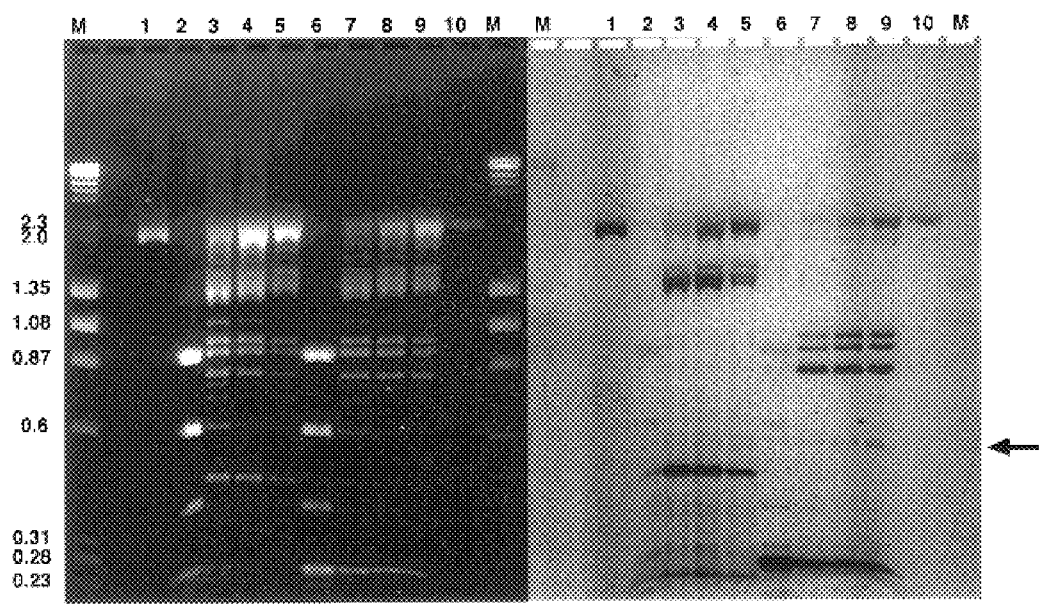
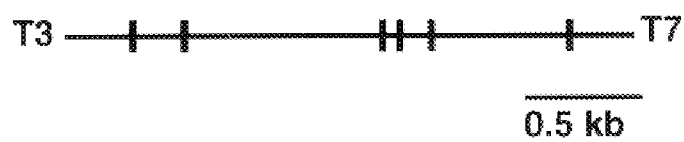

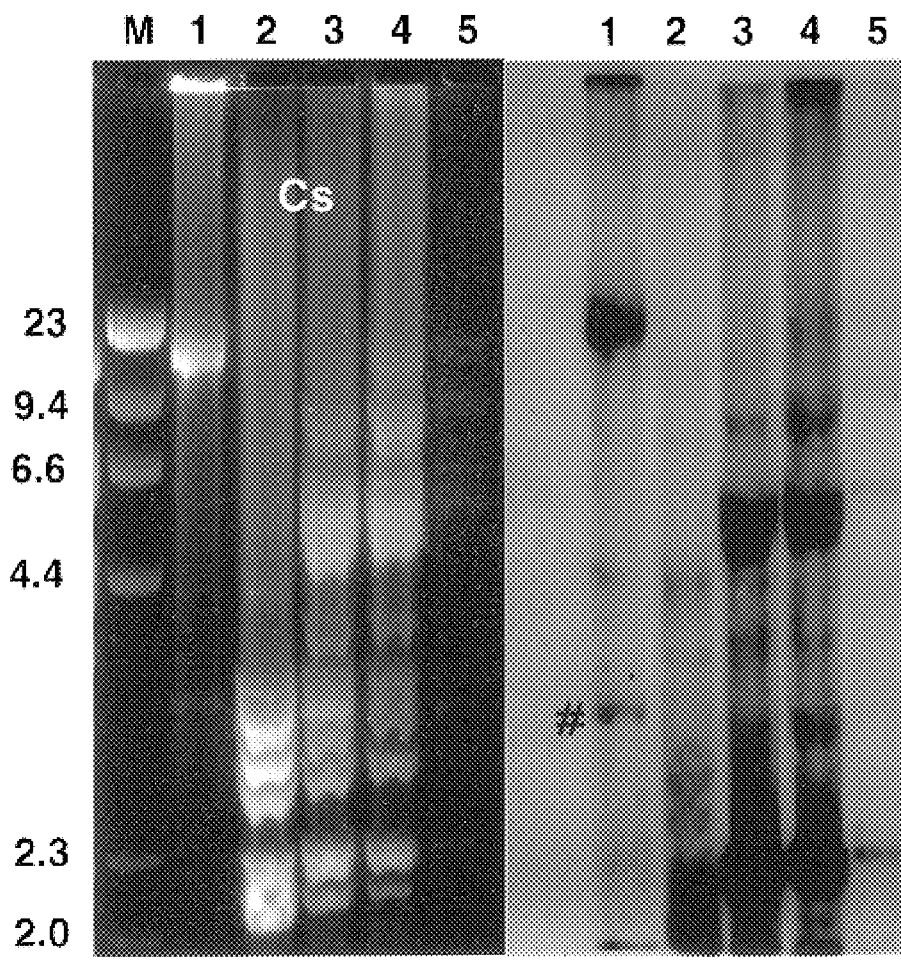

METHODS FOR PRODUCING PARTIALLY DIGESTED RESTRICTION DNA FRAGMENTS AND FOR PRODUCING A PARTIALLY MODIFIED PCR PRODUCT

This invention was made with Government support under Contract DE-AC0676RLO 1830 awarded by the U.S. Department of Energy. The Government has certain rights in the invention.

FIELD OF THE INVENTION

The present invention is related to making a partially modified PCR product that is useful in producing an array of DNA restriction fragments useful for subcloning analysis and for restriction maps. More specifically, the present invention is use of a restriction enzyme site protector permitting use of a complete digestion procedure and obtaining a partial digestion result of an array of restriction fragments.

As used herein, the term "partially modified" is defined as modification of less than 100% of modifiable sites.

As used herein, the term PCR product refers to deoxynucleoside triphosphate(s) copies derived from the DNA template.

BACKGROUND OF THE INVENTION

Subcloning analysis and generation of restriction maps are useful DNA analytical tools. In order to obtain them, one or more DNA fragments is/are partially digested to produce an array of restriction fragments. Partial digestion has also been used for the detection of polymorphisms of various known genetic loci in different organisms (1). Traditional partial digestions require either the termination of restriction digestion reactions at various time points or the use of a limiting restriction enzyme, (2) or the use of specific cloning vectors (3). A more sophisticated method is the combined use of dam methylase and MboI to create partial digestion (4). A disadvantage is that the methylase method requires careful and detailed studies to determine the ratio of the two enzymes to be used for each combination of a DNA methylase and a restriction endonuclease.

The combination of PCR with 5-methyl-dCTP has been used to obtain substrates for assaying the sensitivity of different restriction enzymes towards fully methylated DNA templates (5). In this procedure, dCTP is fully replaced by 5-methyl dCTP in the polymerase chain reaction (PCR). which is not administered until after the PCR is complete. This method generates fully methylated PCR products. However, this method cannot produce a partially modified PCR product nor can it produce an array of DNA restriction fragments as in a partial digestion.

Accordingly, there is a need in the art of DNA analysis for a method requiring less enzyme specificity, and less time and material for making a partially modified PCR product and for producing the array of DNA restriction fragments.

BACKGROUND REFERENCES

5. Wong, K. K. and McClelland, M. (1991) *Nucleic Acids Res.*, 5, 1081–1085.
2. Danna, A. J. (1980) *Meth. Enzymol*, 65, 449–467.
4. Hoheisel, J. D., Nizetic, D. and Lehrach, H. (1989) *Nucleic Acids Res.*, 17, 9571–9582.
3. Tartof, K. D. and Hobbs, C. A. (1988) *Gene*, 67, 169–182.
1. Nobile, C. and Romeo, G. (1988) *Genomics*, 3, 272–274.

SUMMARY OF THE INVENTION

The present invention is an improved method of making a partially modified PCR product. The partially modified PCR product may be further used in producing an array of DNA restriction fragments (as is obtained from a traditional partial digestion method) from a DNA fragment or template with a polymerase chain reaction (PCR). In a standard PCR process, the DNA fragment or template is combined with starting deoxynucleoside triphosphates, a primer, a buffer and DNA polymerase in a PCR mixture. The PCR mixture is then reacted in the PCR producing copies of the DNA fragment. The improvement of the present invention is adding a modiifier at any step prior to completion of the PCR process thereby randomly and partially modifying the copies of the DNA fragment as the partially modified PCR product. The partially modified PCR product may then be digested with an enzyme that cuts the partially modified PCR product at unmodified sites thereby producing an array of DNA restriction fragments.

In addition to subcloning analysis and generating restriction maps, other applications include generating nested Sau3A deletion clones which are useful for gap closure in a sequencing project by cloning the Sau3A partially-digested PCR products into a BamHl and Smal double digested cloning vector. Further, it may be used as a DNA fingerprint to study phylogenetic relationships among several genetic loci in different subsurface bacterial strains. This method of the present invention is also applicable to any study based upon partial digestion including but not limited to the detection of polymorphisms of various known genetic loci in different organisms. The array of DNA restriction fragments generated from the DNA template may also be used as DNA size markers.

An advantage of the present invention is, unlike the methylase process, the extent of methylation in the PCR products may be controlled either by the ratio of the modifier to the corresponding deoxynucleoside triphosphate base, or the sequence of addition of the modifier (ie beginning, middle or end of a PCR reaction). Another advantage is that the partially modified array may be digested with any modifier-sensitive enzyme to create a partial digestion.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

BRIEF DESCRIPTION OF THE DRAWINGS

FIG 1A. Lanes 1 to 5, flourescein-labelled T3 with regular T7 primers; Lanes 6 to 10, regular T3 primer with flourescein-labelled T7 primers. Lanes 1 and lane 10, uncut PCR product; Lanes 2 and 6, no 5-methyl-dCTP added; Lanes 3 and 7, 100 $\mu$M 5-methyl-dCTP was added; Lanes 4 and 8, 150 $\mu$M 5-methyl-dCTP was added; Lanes 5 and 9, 200 $\mu$M 5-methyl-dCTP was added. M, HindIII-digested lambda DNA and HaeIII-digested φ174 DNA were used as size markers. DNA sizes in kb are shown to the left.

FIG. 1B. Same as FIG. 1*b*, agarose gel but visualized with a band filter 530±30 to detect signal from the fluorescein. An arrow indicated a minor non-specific PCR product.

FIG. 1C. Restriction map of Sau3A sites deduced from the FIG. 1*b*.

FIG. 3A. Lane 1, uncut PCR product; Lane 2, no 5-methyl-dCTP added; Lane 3, 50 µM 5-methyl-dCTP was added; Lane 4, 100 µM 5-methyl-dCTP was added; Lane 5, 150 µM 5-methyl-dCTP was added; M, Hindlil-digested lambda DNA were used as size markers. DNA sizes in kb are shown to the left.

FIG. 3B. Lane definitions are the same as for FIG. 3a. Figure obtained from Southern Blot and fluorescein-labelled fragments were detected with anti-fluorescein-AP antibodies. Arrow indicated the detected flourescein-labelled fragments. #, non-specific PCR fragments.

FIG. 3C. Restriction map of HindIII sites deduced from FIG. 3b.

DESCRIPTION OF THE PREFERRED EMBODIMENT(S)

Figure 2:
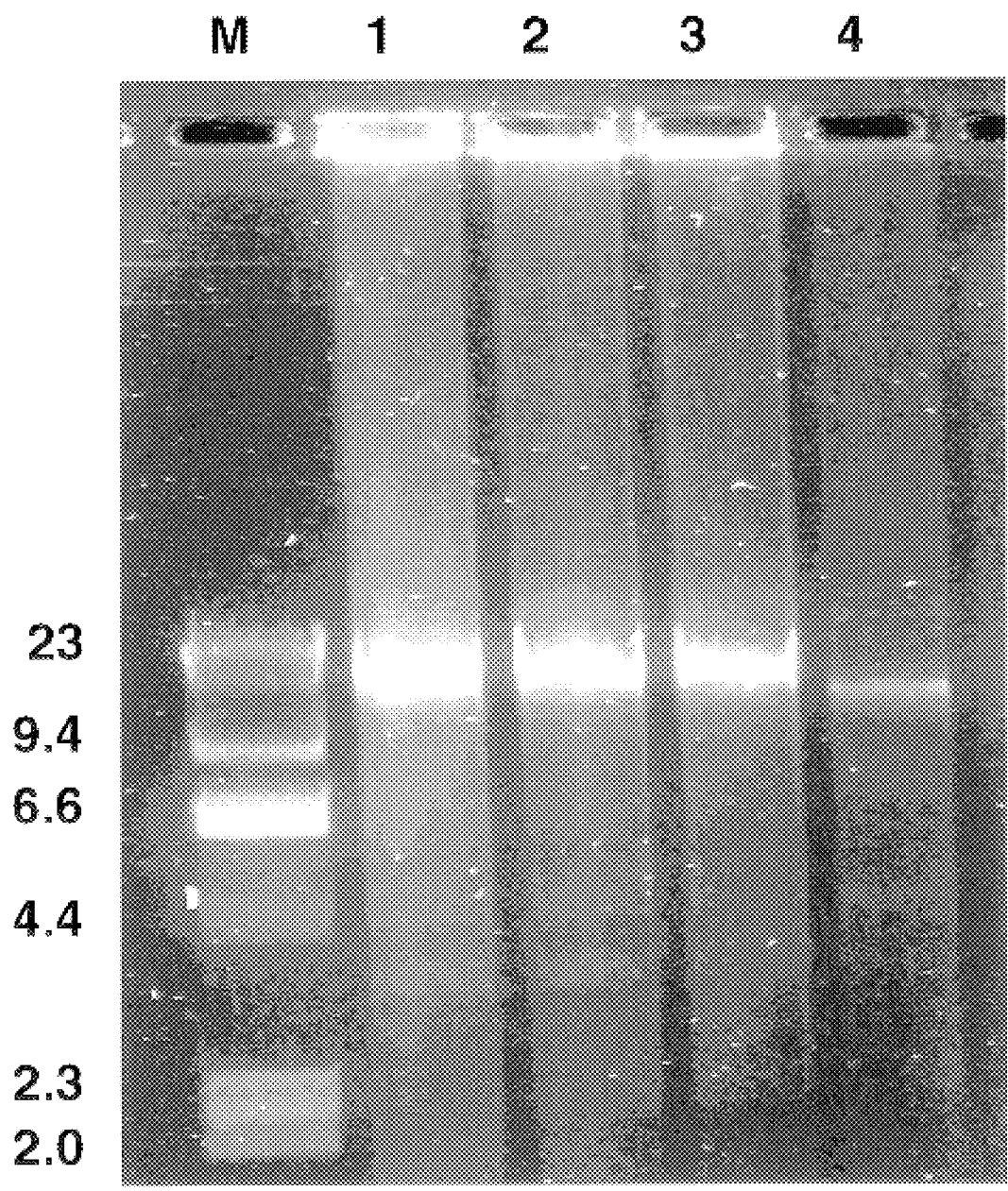
FIG. 2. Lane 1, no 5-methyl-dCTP added; Lane 2, 50 $\mu$M 5-methyl-dCTP was added; Lane 3, 100 $\mu$M 5-methyl-dCTP was added; Lane 4, 150 $\mu$M 5-methyl-dCTP was added; M, HindIll-digested lambda DNA were used as size markers. DNA sizes in kb are shown to the left.

The present invention is an improvement to the standard method of making a partially modified PCR product from a DNA template with a polymerase chain reaction, wherein the DNA template is combined with starting deoxynucleoside triphosphates including dATP (deoxyadenosine-triphosphate), dTTP (deoxythymidine-triphosphate), dGTP (deoxyguanosine-triphosphate), dITP (deoxyinosine-triphosphate) and dCTP (deoxycytidine-triphosphate), a primer (preferably a pair of primers), a buffer and a DNA polymerase in a polymerase chain reaction mixture, the polymerase chain reaction mixture reacted in the polymerase chain reaction producing copies of the DNA fragment; wherein the improvement is the step of adding a modifier at any step prior to completion of the polymerase chain reaction thereby randomly and partially modifying the copies of the DNA fragment as the partially modified PCR product. The dGTP may be substituted with the precursor dITP or included in combination therewith. These steps may be followed by digesting the partially modified PCR product with an enzyme that cuts the partially modified PCR product at unmodified sites thereby producing an array of DNA restriction fragments. The modifier may be any modifier selected from the group consisting of methyl modifiers including but not limited to 4-methyl-dCTP, 5-methyl-dCTP, 6-methyl-dATP and combinations thereof; non-methyl modifiers including but not limited to 7-AZA-dTTP; and combinations thereof. The amount of modifier (e.g. 5-methyl-dCTP) in proportion to the corresponding deoxynucleoside triphosphate (e.g. dCTP) ranges in a ratio from about 0.1:1 to about 1:1.

Buffer(s) and DNA polymerase(s) for use in PCR are well known and the body of technical literature is relied upon for specific identification of these compounds.

EXAMPLE 1

An experiment was conducted to demonstrate the method of the present invention. The initial DNA fragment used as the DNA template was a 2.2 kb DNA fragment cloned in pBluescript (Stratagene, La Jolla, Calif.) in an amount of 50 ng. In a total volume of 100 µl, 4U of rTth DNA polymerase (Perkin-Elmer Corporation, Foster city, Calif.) was used in the recommended buffer.

The pair of primers used was T7 primer, 5'-GTAATACGACTCACTATAGGGC-3'; and T3 primer, 5'AATTAACCCTCACTAAAGGG-3', in a concentration of 0.5 µM. Each dNTP was in a concentration of 200 µM. Either one of the two primers was labeled with fluorescein (Genosys, Woodlands, Tex.) so flourescein-labelled fragments could be detected.

To generate partially-methylated PCR products, 5-methyl-dCTP (Boehringer Mannehem Corp., Indianapolis, Ind.) was then added in addition to the unmodified dNTPs to a final concentrations of 100 µM, 150 µM, and 200 µM.

PCR products were obtained with the GeneAmp XL PCR Kit (Perkin-Elmer, Norwalk, Conn., USA). Flourescein-labelled fragments were detected with a Fluorlmager Sl (Molecular Dynamics, Sunnyvale, Calif.).

A manual hot start was used to increase specificity by adding the rTth DNA polymerase to each individual reaction tube when the reaction buffer had reached 72° C. The reactions were heated to 72° C. for 10 min and followed by 30 cycles of 94° C. for 30 sec, 45° C. for 1 min and 72° C. for 5 min. Then, each of the 100 µl PCR products were purified with a Centricon-100 (Ambion Inc., Beverly, Mass.) by washing with 2 ml sterile water twice and concentrated into 60 µl water for subsequent restriction digestion.

Purified PCR products (20 to 30 µl) were arbitrarily digested with 5 units of Sau3A (Stratagene, La Jolla, Calif.) at 37° C. for 4 hours to completion. The restriction digestions were analyzed with a 1.2% agarose gel stained with ethidium bromide (FIG. 1a, 1b) and fluorescein detection was without a filter for FIG. 1a and with a band filter 530±30. Partial digestion patterns shown in lane 3 to lane 5 and lane 7 to lane 9 (FIG. 1a) indicated that Sau3A restriction sites of the PCR products were randomly protected from digestion when 5-methyl-dCTP was added to PCR reaction mixtures.

Analysis of the relative band intensities on lanes 3 to 5 or lanes 7 to 9 revealed two interesting properties of the partial digestion patterns. Firstly, the concentration of 5-methyl-dCTP from 100 µM to 200 µM did not affect the general restriction digestion pattern except for the largest band (the uncut, fully protected PCR product), which was more abundant at higher concentration. Thus, a concentration of 100 µM of 5-methyl-dCTP was sufficient to generate a partial digestion pattern. Secondly, some of the bands are more abundant. These bands, which appeared darker in the partial digestion patterns, are likely to be fragments derived from PCR products which were only cut once by Sau3A. These fragments were tagged with either T3 or T7 primers as confirmed by detecting fluorescent signals generated from the flourescein-labelled restriction fragments (FIG. 1b). These relatively abundant fragments were all tagged with either T3 or T7 primer at one of their ends. From the sizes of the fluorescein-labeled primer, a restriction map for Sau3A was deduced (FIG. 1c).

EXAMPLE 2

An experiment was conducted to demonstrate the method of the present invention with larger fragments. Partial digestions from 3 kb, 4 kb, 11 kb (data not shown) and 18 kb fragment of a lambda DASHII clone (FIG.'s 2 and 3a, 3b) were done. Fluorescein-labeled T3 and regular T7 primers were used. For FIG. 2, Analysis of restriction fragments was in a 0.7% agarose gel, stained with ethidium bromide. Unlike amplification with smaller fragments, the yield of the 18 kb fragment decreased dramatically when the concentration of 5-methyl-dCTP was increased to 150 µM (FIG. 2, lane 4). Digestion of the 18 kb PCR products completely with Hindlil produced partial restriction patterns (FIG. 3a, 3b) with similar observations as described above. However, the fluorescent signals from the fragments labelled with fluorescein were very weak when detected directly with the Fluorlmager, which were probably due to the quenching effect of longer DNA fragment and less DNA molecules of larger fragments for the same amount of DNA. Thus, Southern blot and detection of fluorescein-labeled fragments with anti-fluorescein-AP antibodies was perfomed (FIG. 3b). A restriction map (FIG. 3C) was also obtained.

CLOSURE

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

I claim:

1. A method of producing an array of DNA restriction fragments from a DNA template with a polymerase chain reaction, wherein the DNA template is combined with starting deoxynucleoside triphosphates, a primer, a buffer and a DNA polymerase in a polymerase chain reaction mixture, the polymerase chain reaction mixture reacted in the polymerase chain reaction producing copies of the DNA template; wherein the improvement comprises:

(a) randomly and partially modifying the copies of the DNA template with a modifier, thereby forming the partially modified PCR product; and (b) digesting the partially modified PCR product with an enzyme that cuts the partially modified PCR product at unmodified sites thereby producing said array of DNA restriction fragments.

2. The method as recited in claim 1, wherein said starting deoxynucleoside triphosphates are selected from the group consisting of dATP, dTTP, dGTP, dITP, dCTP and combinations thereof.

3. The method as recited in claim 1, wherein said modifier is selected from the group consisting methyl modifier, non-methyl modifier and combinations thereof.

4. The method as recited in claim 3, wherein said methyl modifier is selected from the group consisting of 4-methyl-dCTP, 5-methyl-dCTP, 6-methyl-dATP, and combinations thereof.

5. The method as recited in claim 3, wherein said non-methyl modifier is 7-AZA-dTTP.

6. The method as recited in claim 1, wherein said modifier is added at any step prior to completion of the polymerase chain reaction.

7. The method as recited in claim 1, wherein a ratio of said modifier to a corresponding deoxynucleoside triphosphate base is from about 0.1:1 to about 1:1.

8. The method as recited in claim 1, wherein said primer is a pair of primers.

9. The method as recited in claim 8, wherein a one of said pair of primers is labeled with a fluorescent dye.

10. The method as recited in claim 9, wherein said fluorescent dye is fluorescein.

11. A method of making a partially modified PCR product from a DNA template with a polymerase chain reaction, wherein the DNA template is combined with starting deoxynucleoside triphosphates, a primer, a buffer and a DNA polymerase in a polymerase chain reaction mixture, the polymerase chain reaction mixture reacted in the polymerase chain reaction producing copies of the DNA template; wherein the improvement comprises:

randomly and partially modifying the copies of the DNA template with a methyl modifier selected from the group consisting of 4-methyl-dCTP, 5-methyl dCTP, 6-methyl-dATP and combinations thereof, or 7-AZA-dCTP thereby forming the partially modified PCR product.

12. The method as recited in claim 11, further comprising digesting the partially modified PCR product with an enzyme that cuts the partially modified PCR product at unmodified sites thereby producing an array of DNA restriction fragments.

13. The method as recited in claim 11, wherein said modifier is added at any step prior to completion of the polymerase chain reaction.

14. The method as recited in claim 11, wherein a ratio of said modifier to a corresponding deoxynucleoside triphosphate base is from about 0.1:1 to about 1:1.

15. The method as recited in claim 11, wherein said primer is a pair of primers.

16. The method as recited in claim 15, wherein a one of said pair of primers is labeled with a fluorescent dye.

17. The method as recited in claim 16, wherein said fluorescent dye is fluorescein.

* * * * *